United States Patent [19]

Sivik et al.

[11] Patent Number: 5,543,083
[45] Date of Patent: Aug. 6, 1996

[54] FATTY AMINE DERIVATIVES OF BUTYLATED HYDROXY TOLUENE FOR THE PROTECTION OF SURFACES FROM PHYSICAL AND CHEMICAL DEGRADATION

[75] Inventors: Mark R. Sivik, Fairfield; John C. Severns, West Chester, both of Ohio

[73] Assignee: The Procter & Gamble Company, Cincinnati, Ohio

[21] Appl. No.: 280,685

[22] Filed: Jul. 26, 1994

[51] Int. Cl.⁶ .................................................. C09K 15/00
[52] U.S. Cl. ...................... 252/403; 252/404; 252/8.61; 134/40; 134/42; 560/88; 560/110; 560/112; 568/716; 564/505; 564/508
[58] Field of Search .......................... 560/88, 110, 112; 568/716; 564/505, 508; 252/403, 404, 547, 546, 525, 544, 528, 8.8; 134/40, 42

[56] References Cited

U.S. PATENT DOCUMENTS

| | | | |
|---|---|---|---|
| 2,767,207 | 10/1956 | Reasenberg et al. | 560/110 |
| 3,175,941 | 3/1965 | Dekker et al. | 514/535 |
| 3,878,229 | 4/1975 | Strobel | 260/404.5 |
| 3,992,434 | 11/1976 | Oppelt et al. | 260/473 |
| 4,069,309 | 1/1978 | Ciaudelli et al. | 424/47 |
| 4,153,744 | 5/1979 | Remley | 427/160 |
| 4,309,566 | 1/1982 | Konz et al. | 560/110 |
| 4,402,974 | 9/1983 | Matier et al. | 514/533 |
| 4,501,912 | 2/1985 | Matier et al. | 560/66 |
| 4,582,855 | 4/1986 | Kam et al. | 514/487 |
| 4,629,682 | 12/1986 | Leppard et al. | 430/372 |
| 4,680,144 | 7/1987 | Conner | 260/501.15 |
| 4,788,054 | 11/1988 | Bernhardt et al. | 424/59 |
| 5,110,977 | 5/1992 | Wilson et al. | 430/104 |
| 5,134,223 | 7/1992 | Langer et al. | 528/272 |
| 5,194,472 | 3/1993 | Wilson et al. | 524/238 |
| 5,194,667 | 3/1993 | Oxenrider et al. | 560/87 |
| 5,243,021 | 9/1993 | Langer et al. | 528/272 |
| 5,250,652 | 10/1993 | Langer et al. | 528/125 |

FOREIGN PATENT DOCUMENTS

| | | | |
|---|---|---|---|
| 0165710A1 | 12/1985 | European Pat. Off. | C07C 101/62 |
| 0273011A2 | 6/1988 | European Pat. Off. | C07C 101/18 |
| 0272576A1 | 6/1988 | European Pat. Off. | C07C 93/20 |
| 0374751A2 | 12/1988 | European Pat. Off. | B41M 7/02 |
| 0523956A2 | 1/1993 | European Pat. Off. | C11D 3/37 |
| 0523955A2 | 1/1993 | European Pat. Off. | C08G 69/44 |
| 2256612 | 2/1990 | Japan . | |
| 41472 | 4/1992 | Japan . | |
| 2081716 | 2/1982 | United Kingdom | C07C 97/10 |

OTHER PUBLICATIONS

CA 87:24204 (reg. 61604–49–7 and 61631–30–9).
Derwent 92–108725/14 (JP4–41472).
Derwent 90–357443/48 (JP-2-256612).
Textile Chemist and Colorist, "Evaluating UV Absorbers for Museum Textiles", Nov. 1987, vol. 19, No. 11.
Polymer Degradation and Stability 10, "Ultraviolet Absorbers for Retarding Wool Photodegradation: Sulphonated 2–Hydroxybenzophenones and 2,2'–Dihydroxybenzophenones", (1985), pp. 335–352.
Cosmetics and Toiletries, "Encyclopedia of UV Absorbers for Sunscreen Products", vol. 107, Oct. 1992, pp. 45–64.

Primary Examiner—Sharon Gibson
Assistant Examiner—Valerie Fee
Attorney, Agent, or Firm—Thomas G. Krivulka

[57] ABSTRACT

The present invention relates to non-surface staining, light stable antioxidant compounds which reduce the fading, decoloration and degradation of various surfaces, ie., fabrics, from sunlight. These antioxidant compounds are butylated hydroxytoluene and sorbic acid derivatives, containing at least one $C_8$–$C_{22}$ hydrocarbon fatty amine organic moiety and are either solid materials having a melting point of less than about 80° Celsius, or are liquids at a temperature of less than about 40° Celsius.

11 Claims, No Drawings

FATTY AMINE DERIVATIVES OF BUTYLATED HYDROXY TOLUENE FOR THE PROTECTION OF SURFACES FROM PHYSICAL AND CHEMICAL DEGRADATION

TECHNICAL FIELD

The present invention relates to novel, non-surface staining, light stable antioxidant compounds to reduce the fading, discoloration and degradation of various surfaces, i.e. fabrics, from sunlight. These antioxidant compounds are butylated hydroxytoluene and sorbic acid derivatives, preferably containing at least one $C_8$–$C_{22}$ hydrocarbon fatty amine organic moiety and are either solid materials having a melting point of less than about 80° C., or are liquids at a temperature of less than about 40° C. Preferably these antioxidant compounds are incorporated into fabric softening compositions.

BACKGROUND OF THE INVENTION

Consumers worldwide experience color damage to their clothing, upholstery, the interior of their automobiles, etc., from exposure to the sun. For example, color damage to clothing during drying and during wear is especially severe for those consumers living in tropical and subtropical climates. Despite extensive efforts by the industry to develop light stable surfaces such as upholstery, and automobile interiors, to develop light stable dyes, after-treatments to improve light-fastness of dyes for textiles, and plastics which resist fading, the fading of surfaces from sunlight still remains a problem.

Antioxidant compounds are known in the art for various benefits. For example, EPA 273,011, Ravichandran et al., published Jun. 29, 1988, Ciba-Geigy, teaches N,N-bis(hydroxyethyl)hydroxylamine esters to stabilize organic materials (i.e. organic polyolefins, elastomers and lubricating oils) against oxidative, thermal and actinic degradation.

U.S. Pat. No. 5,081,280, Takee et al., issued on Jan. 14, 1992, Yoshitomi Pharmaceutical Industries, Ltd., teaches a process for producing esterified, sterically hindered phenolic compounds as an antioxidant for organic materials with decreased reaction times and less discoloration of the compound. These compounds do not contain an amine function as do the compounds of the present invention.

U.S. Pat. No. 3,330,859, Dexter et al., issued Jul. 11, 1967, Geigy Chemical Corporation, teaches sterically hindered phenolic carboxylic acid esters which are useful to stabilize organic materials such as organic polymers and copolymers, lubricating oils of the aliphatic ester type, hydrocarbon material such as gasoline, etc. These compounds do not contain an amine function as do the compounds of the present invention.

U.S. Pat. No. 3,920,729, Sagawa, et al., issued Nov. 18, 1975, Sumitomo Chemical Co., Ltd., teaches sterically hindered phenolic esterified isopropanolamines for the stabilization of organic substances, particularly polyolefins, halogenated vinyl polymers, copolymers of halogenated vinyl and unsaturated polymerizable compound, copolymers of acrylonitrile, butadiene and styrene, polyurethane, polyamides, polyesters, polyacetals, polycarbonates, polystyrene and natural and synthetic rubber. These compounds have methyl groups attached to the beta carbon atom with regard to the nitrogen atom, for enhanced thermal stability with reduced blooming when mixed with a polyolefin.

U.S. Pat. No. 4,305,868, Wheeler et al., issued December 15, 1981, Uniroyla, Inc., teaches sterically hindered phenolic substituted esterbisamides as antioxidants useful for the protection of organic materials such as synthetic and natural rubbers, plastics and petroleum products against oxidative degradation.

Furthermore, U.S. Pat. No. 4,900,469, Clorox, teaches antioxidants in detergents for bleach stability. Antioxidants have been used in softeners and detergents to prevent fabric yellowing and to control malodor. (See, JP 72/116,783, Kao.)

Because antioxidant compounds are expensive, it is desirable to select and utilize the most efficient compounds in order to minimize the cost of formulating with these compounds.

However, it is now recognized that antioxidants adaptable for various other applications are not always satisfactory for other applications such as for use in foods (as a preservative), cosmetics (as a preservative), in rinse added fabric softener compositions, dryer added fabric softener compositions, detergents, fabric pretreatment or spray on products, hard surface cleaners, compositions for use on floor coverings (i.e. carpet, vinyl), automotive upholstery, upholstery, hair care products, vinyl treatments and plastics.

With regard to textiles, it has now been discovered that visible light is responsible for a significant amount of dye fading on clothing. For example, visible light has a higher contribution to fading than UV-A, which has a higher contribution to fading than UV-B. Antioxidants can provide broader sun-fade fabric protection for surfaces than sunscreen agents because antioxidant effectiveness is not dependent upon the absorption of light.

Therefore, an object of the present invention is to provide antioxidant compounds, effective at low levels, which will reduce the rate of degradation and/or discoloration (i.e. sun-fading) of a variety of surfaces.

All of the above patents and patent applications are incorporated herein by reference.

SUMMARY OF THE INVENTION

The present invention relates to novel antioxidant compounds to reduce the physical or chemical degradation or discoloration of surfaces, especially the fading of a variety of surfaces from sunlight, wherein the antioxidant compound is a non-surface staining, light stable compound, preferably containing at least one $C_8$–$C_{22}$ hydrocarbon fatty organic moiety, preferably at least one $C_{12}$–$C_{18}$ hydrocarbon fatty organic moiety; wherein the antioxidant compound is a solid material having a melting point of less than about 80° C., preferably less than about 50° C., or a liquid at a temperature of less than about 40° C.; preferably from about 0° C. to about 25° C.

These antioxidant compounds are derivatives of butylated hydroxytoluene or sorbic acid and are selected from the group consisting of:

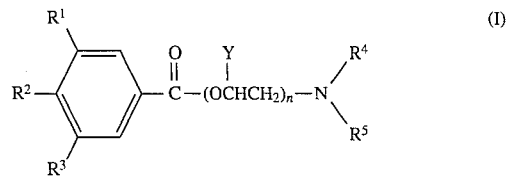

-continued

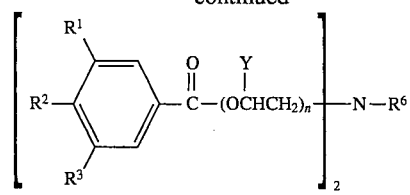
(II)

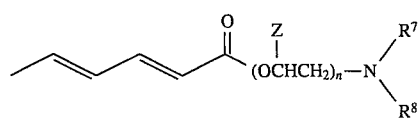
(III)

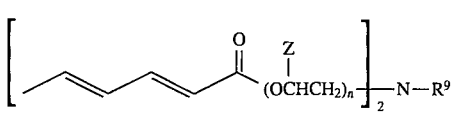
(IV)

wherein each $R^1$ and $R^3$ is selected from the group consisting of hydroxy, methoxy, ethoxy, propoxy, butoxy, methyl, ethyl, propyl, straight or branched chained butyl groups, straight or branched chained amyl groups, and mixtures thereof, preferably straight or branched chained butyl groups, straight or branched chained amyl groups, and mixtures thereof, and more preferably "tert"-butyl groups;

$R^2$ is a hydroxy group;

each $R^4$ and $R^7$ is selected from the group consisting of a saturated or unsaturated $C_1$–$C_{22}$-alkyl, aryl, cyclic alkyl group, (which may be interrupted by an ester, amide, or ether group), hydrogen, and mixtures thereof, preferably a methyl group;

each $R^5$, $R^6$, $R^8$, and $R^9$ is selected from the group consisting of a saturated or unsaturated $C_1$–$C_{22}$, alkyl, aryl, cyclic alkyl group (which may be interrupted by an ester, amide, or ether group), preferably a $C_8$ to C22 alkyl group more preferably a $C_{12}$ to $C_{18}$ alkyl group, and even more preferably a $C_{12}$ to $C_{14}$ alkyl group, and mixtures thereof;

n is from 1 to 50, preferably from 1 to 10, more preferably 1;

Y is a hydrogen or a methyl group; and

Z is a hydrogen or a methyl group.

The amino group of the compounds of Formulas I to IV can be protonated or quaternized with $R^{10}X$ wherein $R^{10}$ is a hydrogen, a $C_1$ to $C_6$ alkyl group, a $C_1$ to $C_6$ hydroxy alkyl group, preferably a $C_1$ to $C_3$ alkyl group or hydroxy alkyl group, e.g. methyl (most preferred), ethyl, propyl, hydroxyethyl, and the like, benzyl group, and mixtures thereof; and $X^-$ is the anion of a strong acid, for example chloride, bromide, methylsulfate, formate, sulfate, nitrate, and the like.

All percentages and ratios used herein are by weight of the total composition.

DETAILED DESCRIPTION OF THE INVENTION

The present invention relates to novel antioxidant compounds to reduce the physical or chemical degradation or discoloration of surfaces, especially the fading of a variety of surfaces from sunlight, wherein the antioxidant compound is a non-surface staining, light stable compound, preferably containing at least one $C_8$–$C_{22}$ hydrocarbon fatty organic moiety, preferably at least one $C_{12}$–$C_{18}$ hydrocarbon fatty organic moiety; wherein the antioxidant compound is a solid material having a melting point of less than about 80° C., preferably less than about 50° C., or a liquid at a temperature of less than about 40° C.; preferably from about 0° C. to about 25° C.

These antioxidant compounds are derivatives of butylated hydroxytoluene or sorbic acid and are selected from the group consisting of:

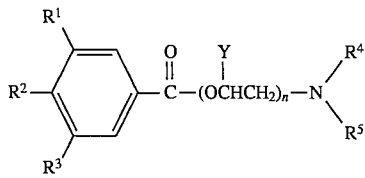
(I)

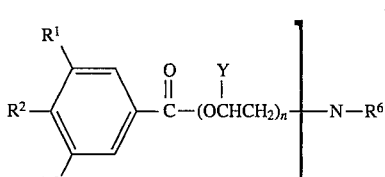
(II)

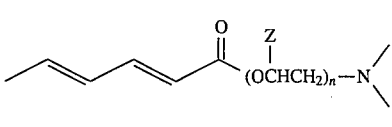
(III)

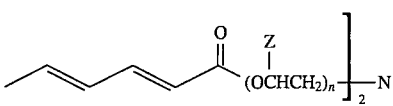
(IV)

wherein each $R^1$ and $R^3$ is selected from the group consisting of hydroxy, methoxy, ethoxy, propoxy, butoxy, methyl, ethyl, propyl, straight or branched chained butyl groups, straight or branched chained amyl groups, and mixtures thereof, preferably straight or branched chained butyl groups, straight or branched chained amyl groups, and mixtures thereof, and more preferably "tert"-butyl groups;

$R^2$ is a hydroxy group;

each $R^4$ and $R^7$ is selected from the group consisting of a saturated or unsaturated $C_1$–$C_{22}$, alkyl, aryl, cyclic alkyl group, (which may be interrupted by an ester, amide, or ether group), hydrogen, and mixtures thereof, preferably a methyl group;

each $R^5$, $R^6$, $R^8$, and $R^9$ is selected from the group consisting of a saturated or unsaturated $C_1$–$C_{22}$, alkyl, aryl, cyclic alkyl group (which may be interrupted by an ester, amide, or ether group), preferably a $C_8$ to $C_{22}$ alkyl group, more preferably a $C_{12}$ to $C_{18}$ alkyl group, and even more preferably a $C_{12}$ to $C_{14}$ alkyl group, and mixtures thereof;

n is from 1 to 50, preferably from 1 to 10, more preferably 1;

Y is a hydrogen or a methyl group; and

Z is a hydrogen or a methyl group.

The amino group can be protonated or quaternized with $R^{10}X$ wherein $R^{10}$ is a hydrogen, a $C_1$ to $C_6$ alkyl group, a $C_1$ to $C_6$ hydroxy alkyl group, preferably a $C_1$ to $C_3$ alkyl group or hydroxy alkyl group, e.g. methyl (most preferred), ethyl, propyl, hydroxyethyl, and the like, benzyl group, and mixtures thereof; and $X^-$ is the anion of a strong acid, for example chloride, bromide, methylsulfate, formate, sulfate, nitrate, and the like.

Preferably each $R^1$ and $R^3$ is a straight or branched chain butyl group and mixtures thereof; $R^4$ is a methyl group; $R^5$ is selected from the group consisting of a saturated or unsaturated $C_{12}$ to $C_{18}$ alkyl group; and n is 1.

More preferably, each $R^1$ and $R^3$ is a "tert"-butyl group; $R^5$ is selected from the group consisting of a saturated or unsaturated $C_{12}$ to $C_{14}$ alkyl group; and n is 1.

An especially preferred compound of the present invention is 2-(N-methyl-N-cocoamino)ethyl 3', 5'-di-tert-butyl-4-hydroxybenzoate.

The antioxidant compounds of the present invention demonstrate light stability. "Light stable" means that the antioxidant compounds of the present invention do not discolor when exposed to either sunlight or simulated sunlight for approximately 2 to 60 hours at a temperature of from about 25° C. to about 45° C.

Antioxidant compounds and free radical scavengers can generally stabilize surfaces and/or protect dyes from degradation or discoloration by first preventing the generation of singlet oxygen and peroxy radicals, and thereafter terminating the degradation pathways. Not to be limited by theory, a general discussion of the mode of action for antioxidants and free radical scavengers is disclosed in Kirk Othmer, The Encyclopedia of Chemical Technology, Volume 3, pages 128–148, Third Edition (1978), which is incorporated herein by reference in its entirety.

Methods of Manufacture

The following examples further describe and demonstrate embodiments within the scope of the present invention. The examples are given solely for the purpose of illustration and are not to be construed as limitations of the present invention, as many variations thereof are possible without departing from the spirit and scope of the invention.

EXAMPLE 1

N-methyl-N-(2-hydroxyethyl)cocoamine in the amount of 15.64 g (63.3 mmol) is dissolved in 200 mL of dichloromethane and the resulting solution heated to 40° C. Following addition of triethylamine in the amount of 6.41 g (63.3 mmol), 3,5-di-tert-butyl-4-hydroxybenzoyl chloride in the amount of 17.00 g (63.3 mmol) is added to the solution so as to maintain the reaction temperature at 35°–40° C. The reaction mixture is stirred for an additional 2 h at 40° C. and then cooled to room temperature. After stirring 16 h, the solution containing the reaction product is filtered and the filtrate concentrated. The resulting residue is re-dissolved in 300 mL of chloroform and washed twice with two 50 mL aliquots of 50% $K_2CO_3$ in water. The organic layer is separated, dried over $MgSO_4$, filtered, and concentrated. The product is purified by column chromatography. Purity of the product is determined by thin layer chromatography and the structure confirmed by $^{13}C$ NMR.

EXAMPLE 2

N,N-bis-(2-hydroxyethyl)-cocoamine in the amount of 22.09 g (78.1 mmol) and triethylamine in the amount of 15.79 g (156.3 mmol) are dissolved in 100 mL of dichloromethane. The resulting solution is treated with 3,5-di-tert-butyl- 4-hydroxybenzoyl chloride in the amount of 42.00 g (156.3 mmol) dissolved in 100 mL of dichloromethane. During addition the reaction temperature is maintained between 35°–400° C. The reaction mixture is stirred for an additional 60 min at reflux and then cooled to room temperature. The mixture is filtered and the filtrate concentrated. The resulting residue is redissolved in 200 mL of dichloromethane and washed twice with two 100 mL aliquots of 50% $K_2CO_3$ in water, once with 100 mL of saturated $NaHCO_3$ solution in water, and once with 100 mL of brine. The organic layer is separated, dried over $MgSO_4$, filtered, and concentrated to give a viscous oil. Purity of the product is determined by thin layer chromatography and the structure confirmed by $^{13}C$ NMR.

EXAMPLE 3

N-methyl-N-(2-hydroxyethyl)cocoamine in the amount of 36.28 g (144.0 mmol) and triethylamine in the amount of 14.62 g (144.0 mmol) are dissolved in 250 mL of dichloromethane. The resulting solution is treated with 2,4-trans-trans-hexandienoyl chloride in the amount of 18.80 g (144.0 mmol). During addition, the reaction temperature is maintained between 35°– 40° C. The reaction mixture is stirred for an additional 2 h at reflux and then cooled to room temperature. The mixture is filtered and the filtrate concentrated. The resulting residue is re-dissolved in 300 mL of dichloromethane and washed twice with 200 mL of 50% $K_2CO_3$ in water and twice with 200 mL of saturated $NaHCO_3$ solution in water. The organic layer is separated, dried over $MgSO_4$, treated with activated charcoal, filtered, and concentrated to give an oil. Purity of the product is determined by thin layer chromatography and the structure confirmed by $^{13}C$ NMR.

COMPOSITIONS

The present invention also relates to a composition for decreasing the physical or chemical degradation of surfaces, comprising:

(A) an effective amount of an antioxidant compound; and (B) an effective amount of a carrier material; wherein the antioxidant compound is selected from the group consisting of:

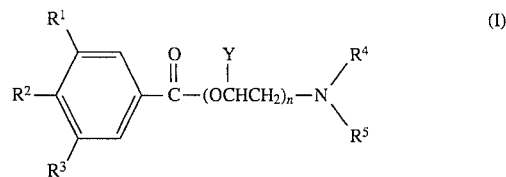
(I)

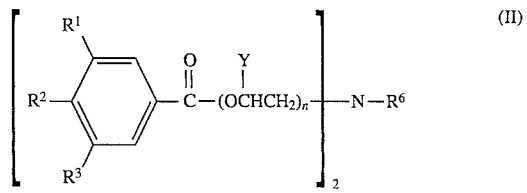
(II)

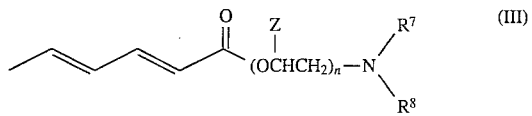
(III)

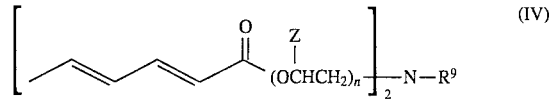
(IV)

wherein each $R^1$ and $R^3$ is selected from the group consisting of hydroxy, methoxy, ethoxy, propoxy, butoxy, methyl, ethyl, propyl, straight or branched chained butyl groups, straight or branched chained amyl groups, and mixtures thereof, preferably straight or branched chained butyl groups, straight or branched chained amyl groups, and mixtures thereof, and more preferably "tert"-butyl groups;

$R^2$ is a hydroxy group;

each $R^4$ and $R^7$ is selected from the group consisting of a saturated or unsaturated $C_1$–$C_{22}$, alkyl, aryl, cyclic alkyl group (which may be interrupted by an ester, amide, or ether group), hydrogen, and mixtures thereof, preferably a methyl group;

each $R^5$, $R^6$, $R^8$, and $R^9$ is selected from the group consisting of a saturated or unsaturated $C_1$–$C_{22}$, alkyl, aryl, cyclic alkyl group (which may be interrupted by an ester, amide, or ether group), preferably a $C_8$ to $C_{22}$ alkyl group, more preferably a $C_{12}$ to $C_{18}$ alkyl group, and even more preferably a $C_{12}$ to $C_{14}$ alkyl group, and mixtures thereof;

n is from 1 to 50, preferably from 1 to 10, more preferably 1;

Y is a hydrogen or a methyl group; and

Z is a hydrogen or a methyl group.

The amino group can be protonated or quaternized with $R^{10}X$ wherein $R^{10}$ is a hydrogen, a $C_1$ to $C_6$ alkyl group, a $C_1$ to $C_6$ hydroxy alkyl group, preferably a $C_1$ to $C_3$ alkyl group or hydroxy alkyl group, e.g. methyl (most preferred), ethyl, propyl, hydroxyethyl, and the like, benzyl group, and mixtures thereof; and $X^-$ is the anion of a strong acid, for example chloride, bromide, methylsulfate, formate, sulfate, nitrate, and the like.

The carrier and/or diluent employed in the instant compositions is a non-toxic, non-irritating substance which when mixed with the antioxidant compound, promotes the deposition of the antioxidant compound onto surfaces. The compositions of the present invention preferably comprise from about 25% to about 95%, preferably from about 50% to about 90% of a liquid carrier. Preferably the carrier and/or diluent is primarily water due to its low cost relative availability, safety, and environmental compatibility. The level of water in the liquid carrier is at least about 50%, preferably at least about 60%, by weight of the carrier. Mixtures of water and low molecular weight, e.g., <100 g/mol, organic solvent, e.g., lower alcohol such as ethanol, propanol, isopropanol or butanol are useful as the carrier liquid. Low molecular weight alcohols include monohydric, dihydric (glycol, etc.) trihydric (glycerol, etc.), and higher polyhydric (polyols) alcohols.

What is claimed is:

1. An antioxidant compound, to reduce the degradation or discolorntion of surfaces from sunlight, selected from the group consisting of:

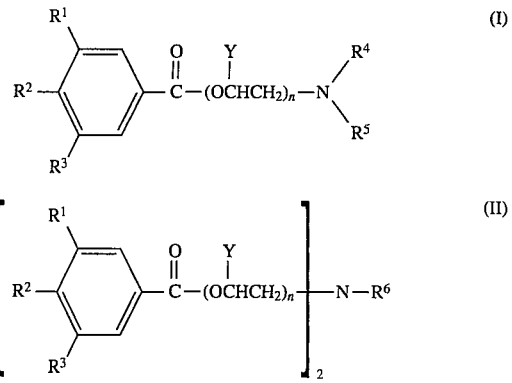

and mixtures thereof wherein each $R^1$ is selected from the group consisting of hydroxy, methoxy, ethoxy, propoxy, butoxy, methyl, ethyl, propyl, straight or branched chained butyl groups, and straight or branched chained amyl groups;

each $R^2$ is a hydroxy group;

each $R^3$ is selected from the group consisting of hydroxy, methoxy, ethoxy, propoxy, butoxy, methyl, ethyl, propyl, straight or branched chained butyl groups, and straight or branched chained amyl groups;

each $R^4$ is selected from the group consisting of a saturated or unsaturated $C_1$–$C_{22}$ alkyl, aryl, or cyclic alkyl group, and hydrogen;

each $R^5$ is n saturated or unsaturated $C_1$–$C_{22}$ alkyl, aryl, or cyclic alkyl group;

each $R^6$ is a saturated or unsaturated $C_1$–$C_{22}$, alkyl, aryl, or cyclic alkyl group;

n is from 1 to 50;

Y is a hydrogen or a methyl group; and wherein the amino group of the compounds of Formulas I to II, optionally, quaternized with $R^{10}X$ when $R^{10}$ is a hydrogen, a $C_1$–$C_6$ alkyl group, a $C_1$–$C_6$ hydroxyl alkyl group, benzyl group; and X is an anion from a strong acid.

2. The antioxidant compound of claim 1 wherein the antioxidant compound is a solid material having a melting point of less than about 80° C. or a liquid at a temperature of less than about 40° C.

3. The antioxidant compound of claim 1 wherein the antioxidant compound is a solid material having a melting point of less than about 50° C. or a liquid at a temperature of about 0° C. to about 25° C.

4. The antioxidant compound of claim 3 wherein the compound is 2-(N-methyl-N-cocoamino)ethyl 3',5'-di-tert-butyl-4-hydroxybenzoate.

5. The antioxidant compound of claim 1 wherein each $R^1$ and $R^3$ is a straight or branched chain butyl group, straight or branched chained amyl group, and mixtures thereof; $R^4$ is a methyl group; each $R^5$ and $R^6$ is a saturated or unsaturated $C_{12}$ to $C_{14}$ alkyl group.

6. The antioxidant compound of claim 5 wherein each $R^1$ and $R^3$ is a "tert"-butyl group; each $R^5$ and $R^6$ is a saturated or unsaturated $C_{12}$ to $C_{14}$ alkyl group.

7. The antioxidant compound of claim 6 wherein the antioxidant compound is selected from the group consisting of Formula I, Formula II and mixtures thereof wherein each $R^1$ and $R^3$ is a "tert"-butyl group; each $R^5$ and $R^6$ is a saturated or unsaturated $C_{12}$ to $C_{14}$ alkyl group.

8. The antioxidant compound of claim 7 wherein the antioxidant compound is 2-(N-methyl-N-cocoamino)ethyl 3,5-di-tert-butyl-4-hydroxybenzoate.

9. A composition for decreasing the physical or chemical degradation of surfaces, comprising:

(A) an effective amount for decreasing the physical or chemical degradation of surfaces, of the antioxidant compound of claim 1; and (B) from about 25% to about 95%, by weight of the composition, of a carrier material.

10. A composition for decreasing the physical or chemical degradation of surfaces, composing:

(A) an effective amount for decreasing the physical or chemical degradation of surfaces, of the antioxidant compound of claim 8; and (B) from about 25% to about 95%, by weight of the composition, of a carrier material.

11. A composition for decreasing the physical or chemical degradation of surfaces, comprising:

(A) an effective amount for decreasing the physical or chemical degradation of surfaces, of the antioxidant compound of claim 1; and (B) from about 25% to about 95%, by weight of the composition, of a carrier material.

* * * * *